United States Patent

Takeda et al.

[11] Patent Number: 4,594,342
[45] Date of Patent: Jun. 10, 1986

[54] 1,5-BENZOTHIAZEPINE DERIVATIVE

[75] Inventors: Mikio Takeda, Urawa; Tokuro Oh-ishi, Tokyo; Hiromichi Nakajima, Urawa; Taku Nagao, Tokyo, all of Japan

[73] Assignee: Tanabe Seiyaku Co., Ltd., Japan

[21] Appl. No.: 715,115

[22] Filed: Mar. 22, 1985

[30] Foreign Application Priority Data

Apr. 10, 1984 [GB] United Kingdom ................ 8409259
Apr. 28, 1984 [GB] United Kingdom ................ 8410949

[51] Int. Cl.[4] .................... A61K 31/55; C07B 281/10
[52] U.S. Cl. .............................. 514/211; 260/239.3 B
[58] Field of Search ................ 260/239.3 B; 514/211

[56] References Cited

U.S. PATENT DOCUMENTS

| 3,075,967 | 1/1963 | Krapcho | 260/239.3 B |
| 3,341,519 | 9/1967 | Krapcho | 260/239.3 B |
| 3,562,257 | 2/1971 | Kugita et al. | 260/239.3 B |

FOREIGN PATENT DOCUMENTS

| 81234A1 | of 1983 | European Pat. Off. | 260/239.3 B |
| 56-156217 | 12/1981 | Japan | 260/239.3 B |
| 56-156218 | 12/1981 | Japan | 260/239.3 B |

OTHER PUBLICATIONS

Murphy et al., "Proc. Natl. Acad. Sciences (USA) (1983), vol. 80, No. 3, pp. 860–861.
Chemical Abstracts, vol. 99, (1983), Item 476897p, abstracting "Circulation Res. Supp.", (1983), vol. 52, No. 1, pp. 115–119, (Kiyomoto et al.).
"Circulation Research Supp. I.," Calcium Channel—Blocking Drugs, vol. 52, pp. I-115-I-119, 1983, (Kiyomoto, et al.).

*Primary Examiner*—Robert T. Bond
*Attorney, Agent, or Firm*—Scully, Scott, Murphy & Presser

[57] ABSTRACT

Novel 1,5-benzothiazepine derivatives of the formula:

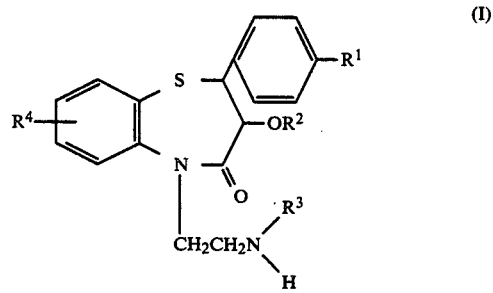

wherein
$R^1$ and $R^4$ are:
(a) $R^1$ is lower alkyl or lower alkoxy, and $R^4$ is lower alkyl, lower alkoxy, fluorine, benzyloxy, hydroxy or lower alkylthio, or
(b) $R^1$ is lower alkyl, and $R^4$ is hydrogen, or
(c) $R^1$ is hydroxy, and $R^4$ is lower alkyl, fluorine, hydroxy or lower alkylthio;
$R^2$ is hydrogen, lower alkanoyl or benzoyl; and $R^3$ is lower alkyl; and a pharmaceutically acceptable acid addition salt thereof are disclosed. Said derivative (I) and its salt have a potent platelet aggregation-inhibiting activity.

24 Claims, No Drawings

1,5-BENZOTHIAZEPINE DERIVATIVE

This invention relates to a novel 1,5-benzothiazepine derivative and processes for preparing the same. More particularly, it relates to a compound of the formula:

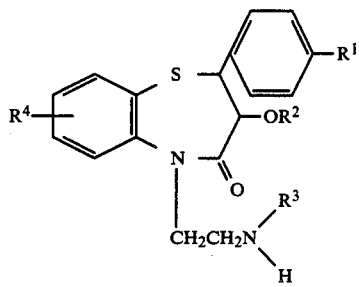

wherein
$R^1$ and $R^4$ are:
(a) $R^1$ is lower alkyl or lower alkoxy, and $R^4$ is lower alkyl, lower alkoxy, fluorine, benzyloxy, hydroxy or lower alkylthio, or
(b) $R^1$ is lower alkyl, and $R^4$ is hydrogen, or
(c) $R^1$ is hydroxy, and $R^4$ is lower alkyl, fluorine, hydroxy or lower alkylthio;

$R^2$ is hydrogen, lower alkanoyl or benzoyl; and $R^3$ is lower alkyl; or a pharmaceutically acceptable acid addition salt thereof.

U.S. Pat. No. 3,562,257 discloses various benzothiazepine derivatives including 7-chloro-1,5-benzothiazepine derivatives such as 2-(4-methoxyphenyl)-3-hydroxy(or acetoxy)-5-[2-(dimethylamino)ethyl]-7-chloro-2,3-dihydro-1,5-benzothiazepin-4(5H)-one. Said U.S. Patent also discloses that these benzothiazepine derivatives have antidepressive, tranquilizing and/or coronary vasodilating activity.

On the other hand, it is known that the interaction of blood constituents, especially platelets and blood coagulation factors, with blood vessel walls is causative of thrombus formation. For example, in damaged blood vessels, circulating blood platelets contact with the exposed subendothelial tissues such as collagen to release blood platelet aggregation-activating substances, and said substances cause circulating platelets to adhere to each other. The platelet aggregates thus formed at the injury site are then stabilized by fibrin, resulting in thrombus formation. Thus, the development of a platelet aggregation-inhibiting agent which suppresses the above-mentioned processes is of great importance in therapeutic treatment of thrombosis.

As a result of various investigations, we have now found that the compound (I) of the present invention or a pharmaceutically acceptable acid addition salt thereof has a potent platelet aggregation-inhibiting activity and is useful as an antithrombotic agent. For example, when the inhibitory effect of a test compound on collagen-induced platelet aggregation in rat or human platelets was estimated in terms of $IC_{50}$ (i.e., concentration of test compound which was required to induce 50% inhibition of collagen-induced platelet aggregation), the $IC_{50}$ of (−)-cis-2-(4-methylphenyl)-3-hydroxy-5-[2-(N-methylamino)ethyl]-8-methyl-2,3-dihydro-1,5-benzothiazepin-4(5H)-one (hydrochloride) was 0.1 μg/ml (rat platelets) or 0.003–0.03 μg/ml (human platelets) whereas said value of acetylsalicylic acid was about 45 μg/ml (rat platelets) or about 20 μg/ml (human platelets).

Representative examples of the compound of the present invention include those of the formula (I) in which $R^1$ is lower alkyl of one to 4 carbon atoms such as methyl, ethyl, propyl or butyl, or lower alkoxy of one to 4 carbon atoms such as methoxy, ethoxy, propoxy or butoxy, and $R^4$ is lower alkyl of one to 4 carbon atoms such as methyl, ethyl, propyl or butyl, lower alkoxy of one to 4 carbon atoms such as methoxy, ethoxy, propoxy or butoxy, fluorine, benzyloxy, hydroxy or lower alkylthio of one to 4 carbon atoms such as methythio, ethylthio, propylthio or butylthio; $R^1$ is lower alkyl of one to 4 carbon atoms, and $R^4$ is hydrogen; or $R^1$ is hydroxy, and $R^4$ is lower alkyl of one to 4 carbon atoms, fluorine, hydroxy or lower alkylthio; $R^2$ is hydrogen, lower alkanoyl of 2 to 5 carbon atoms such as acetyl, propionyl, butyryl, isobutyryl or valeryl, or benzoyl; and $R^3$ is lower alkyl of one to 4 carbon artoms such as methyl, ethyl, propyl or butyl.

Among the compounds of the present invention, a preferred subgenus includes those of the formula (I) in which $R^1$ is lower alklyl or lower alkoxy, and $R^4$ is lower alkyl, lower alkoxy or hydroxy; or $R^1$ is lower alkyl, and $R^4$ is hydrogen; $R^2$ is hydrogen or lower alkanoyl; and $R^3$ is lower alkyl. Another preferred subgenus includes those of the formula (I) in which $R^1$ is lower alkyl or lower alkoxy; $R^2$ is hydrogen or lower alkanoyl; $R^3$ is lower alkyl; and $R^4$ is lower alkyl or hydroxy. Other preferred subgenus includes those of the formula (I) in which $R^1$ is lower alkyl; $R^2$ is hydrogen or lower alkanoyl; $R^3$ is lower alkyl; and $R^4$ is lower alkyl. Still other preferred subgenus includes those of the formula (I) in which $R^1$ is methyl or methoxy, and $R^4$ is methyl, methoxy, fluorine, benzyloxy, hydroxy or methylthio; or $R^1$ is methyl, and $R^4$ is hydrogen; or $R^1$ is hydroxy, and $R^4$ is methyl; $R^2$ is hydrogen, acetyl, propionyl, butyryl, isobutyryl or benzoyl; and $R^3$ is methyl. More preferred subgenus includes those of the formula (I) in which $R^1$ is methyl or methoxy, and $R^4$ is methyl, methoxy or hydroxy; or $R^1$ is methyl, and $R^4$ is hydrogen; $R^2$ is hydrogen or acetyl; and $R^3$ is methyl. Further preferred subgenus includes those of the formula (I) in which $R^1$ is methyl or methoxy; $R^2$ is hydrogen or acetyl; $R^3$ is methyl; and $R^4$ is methyl or hydroxy. Most preferred subgenus includes those of the formula (I) in which $R^1$ is methyl, $R^2$ is hydrogen or acetyl, $R^3$ is methyl, and $R^4$ is methyl and is in the 8-position of benzothiazepine skeleton.

While the compound (I) of the present invention can exist in the form of two diastereoisomers (i.e., cis and trans isomers) or four optical isomers (i.e., (+)-cis, (−)-cis, (+)-trans and (−)-trans isomers) due to the two asymmetric carbon atoms involved therein, all of these isomers or a mixture thereof are included within the scope of the invention. Among said isomers, however, the cis isomer, especially the (−)-cis-isomer, thereof is generally preferred for medicinal use.

According to the present invention, the compound (I) may be prepared by either one of the methods shown in the following reaction schemes:

Method (A)

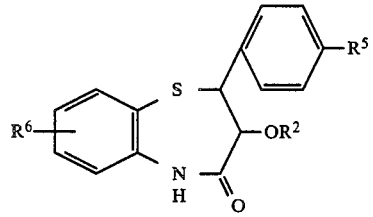
(II)

+

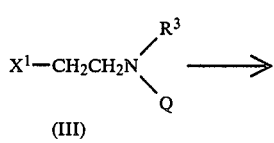
(III)

⟶

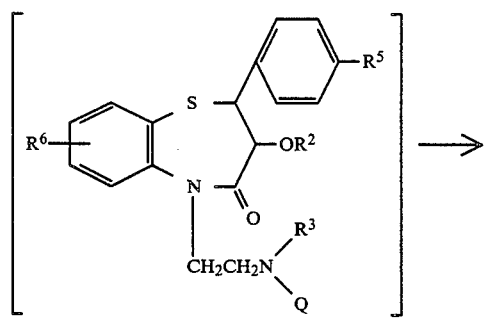
(IV)

⟶

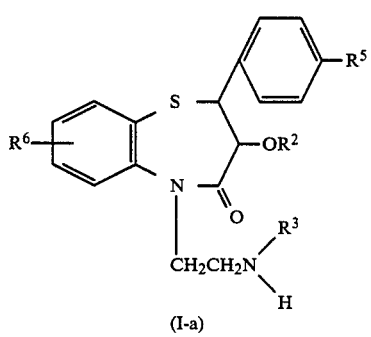
(I-a)

wherein $R^5$ is lower alkyl or lower alkoxy, and $R^6$ is lower alkyl, lower alkoxy, fluorine, benzyloxy or lower alkylthio, or $R^5$ is lower alkyl, and $R^6$ is hydrogen; Q is hydrogen or a protecting group; $X^1$ is halogen; and $R^2$ and $R^3$ are the same as defined above.

Method (B)

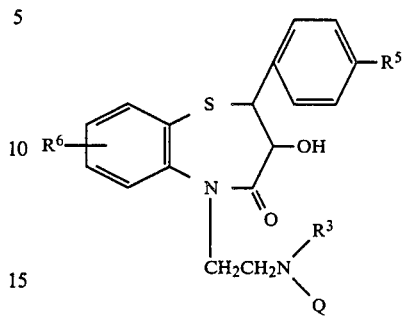
(V)

$R^7COOH$ (VI) or a + reactive derivative thereof ⟶

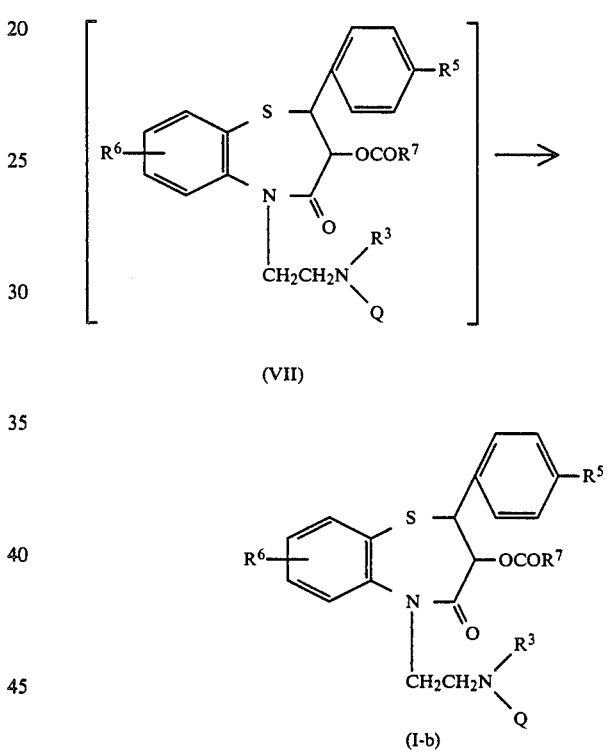
(VII)

⟶

(I-b)

wherein $R^7$ is lower alkyl or phenyl, and $R^3$, $R^5$, $R^6$ and Q are the same as defined above.

Method (C)

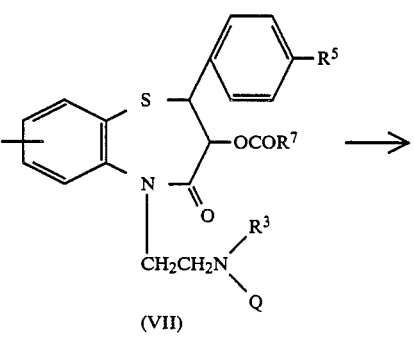
(VII)

⟶

-continued

Method (C)

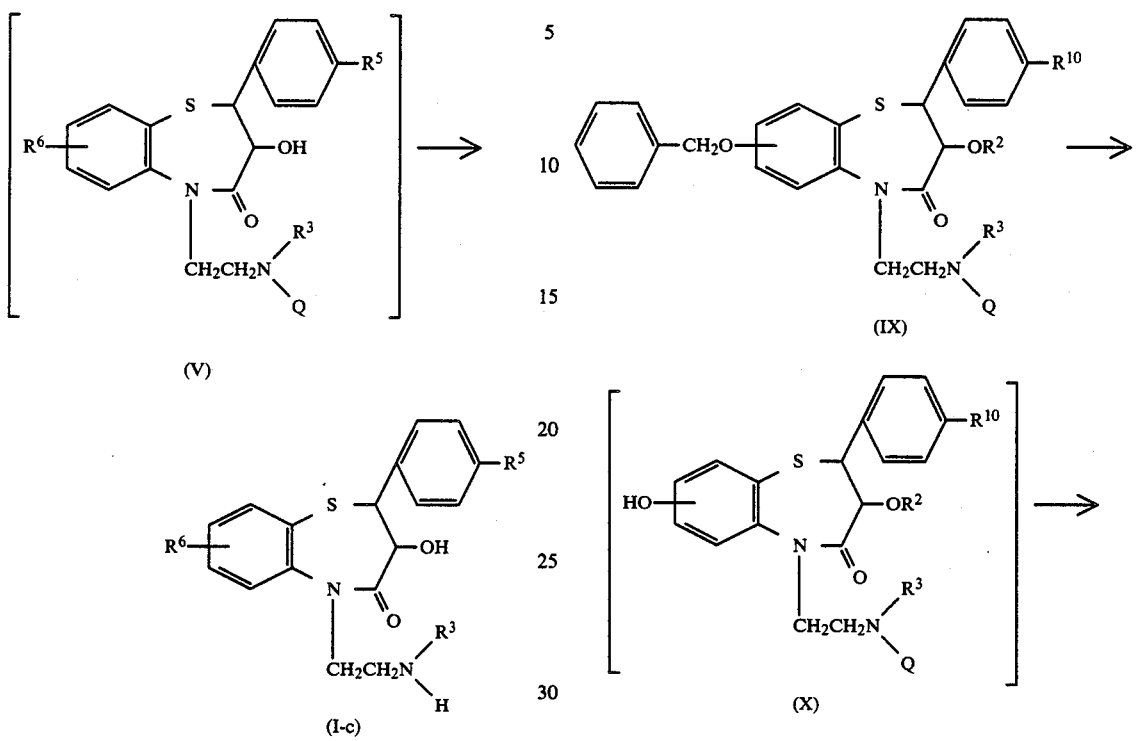

wherein $R^3$, $R^5$, $R^6$, $R^7$ and Q are the same as defined above.

Method (D)

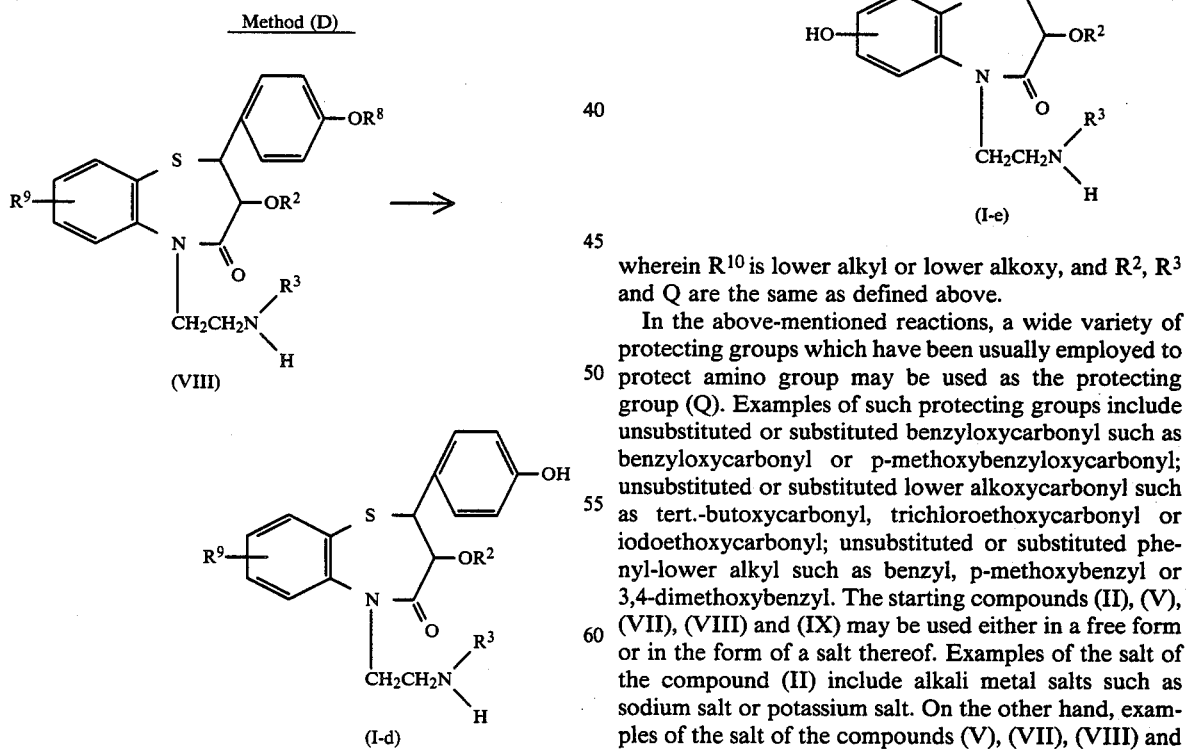

wherein $R^8$ is lower alkyl, $R^9$ is lower alkyl, fluorine, hydroxy or lower alkylthio, and $R^2$ and $R^3$ is the same as defined above.

Method (E)

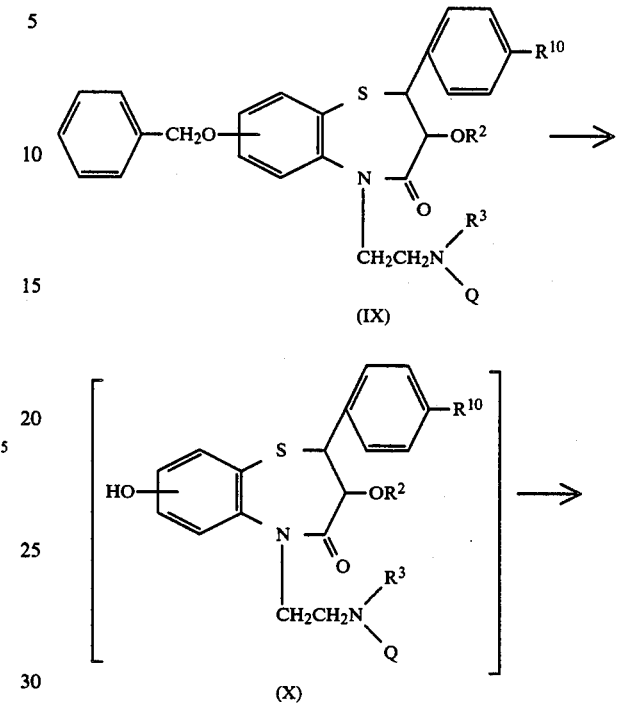

wherein $R^{10}$ is lower alkyl or lower alkoxy, and $R^2$, $R^3$ and Q are the same as defined above.

In the above-mentioned reactions, a wide variety of protecting groups which have been usually employed to protect amino group may be used as the protecting group (Q). Examples of such protecting groups include unsubstituted or substituted benzyloxycarbonyl such as benzyloxycarbonyl or p-methoxybenzyloxycarbonyl; unsubstituted or substituted lower alkoxycarbonyl such as tert.-butoxycarbonyl, trichloroethoxycarbonyl or iodoethoxycarbonyl; unsubstituted or substituted phenyl-lower alkyl such as benzyl, p-methoxybenzyl or 3,4-dimethoxybenzyl. The starting compounds (II), (V), (VII), (VIII) and (IX) may be used either in a free form or in the form of a salt thereof. Examples of the salt of the compound (II) include alkali metal salts such as sodium salt or potassium salt. On the other hand, examples of the salt of the compounds (V), (VII), (VIII) and (IX) include inorganic acid addition salts such as hydrochloride, hydrobromide, perchlorate or hydroiodide, and organic acid addition salts such as oxalate, maleate, fumarate, succinate or methanesulfonate.

According to the method (A), the compound (I-a) may be prepared by condensing the compound (II) or a salt thereof with the compound (III) or a salt thereof to give the compound (IV) and, when Q is a protecting group, further removing said protecting group from the compound (IV).

The condensation reaction of the compound (II) or a salt thereof with the compound (III) or a salt thereof may be carried out in a solvent. When the compound (II) is used in a free form, it is preferred to carry out the reaction in the presence of an alkali agent. The alkali agent includes, for example, alkali metal hydroxide (e.g., potassium hydroxide, sodium hydroxide), alkali metal carbonate (e.g., potassium carbonate, sodium carbonate) and alkali metal hydride (e.g., sodium hydride). Examples of the salt of the compound (III) include acid addition salts thereof such as hydrochloride, hydrobromide and so forth. Acetone, ethyl acetate, dimethylsulfoxide, dimethylformamide and dioxane are suitable as the solvent. It is preferred to carry out the reaction at a temperature of 20° to 100° C., especially at 25° to 70° C.

Removal of the protecting group from the compound (IV) may be conducted in a conventional manner. For example, when the protecting group is a substituted or unsubstituted benzyloxycarbonyl group such as benzyloxycarbonyl or p-methoxybenzyloxycarbonyl, it is preferably removed by treating the compound (IV) with an acid in a solvent. Hydrogen bromide, hydrogen chloride and trichloroacetic acid are preferably used as the acid. Acetic acid, benzene, ethyl acetate, methylene chloride, 1,2-dichloroethane, chloroform, toluene and chlorobenzene are suitable as the solvent. It is preferred to carry out the reaction at a temperature of 0° to 40° C., especially at 0° to 25° C. Tert.-butoxycarbonyl group may also be removed by treating the compound (IV) with an acid in a solvent. Examples of the acid include hydrobromic acid, hydrochloric acid, trifluoroacetic acid and formic acid. Acetic acid and water are suitable as the solvent. It is preferred to carry out the reaction at a temperature of −10° to 50° C., especially 0° to 40° C. $\beta,\beta,\beta$-trichloroethoxycarbonyl group may be removed by treating with zinc-acetic acid at 20° to 60° C. Further, iodoethoxycarbonyl group may be removed by treating with zinc-methanol at 20° to 60° C. When the protecting group is a substituted or unsubstituted phenyl-lower alkyl group (e.g., benzyl, p-methoxybenzyl, 3,4-dimethoxybenzyl), it may be removed by replacing it with a group which can be removed with an acid (e.g., benzyloxycarbonyl), and then removing such replaced protecting group with an acid under the same conditions as above. Replacement of the substituted or unsubstituted phenyl-lower alkyl group with benzyloxycarbonyl group is conducted by reacting the compound (IV) (Q=substituted or unsubstituted phenyl-lower alkyl) with benzyloxycarbonyl halide (e.g., benzyloxycarbonyl chloride) in a solvent. Benzene, toluene, xylene, dioxane and tetrahydrofuran are suitable as the solvent. It is preferred to carry out the reaction at a temperature of 50° to 130° C., especially at 80° to 100° C.

According to the method (B), the compound (I-b) may be prepared by condensing the compound (V) or a salt thereof with the compound (VI) or a reactive derivative thereof to give the compound (VII) and, when Q is a protecting group, further removing said protecting group from the compound (VII).

The starting compound (V) corresponds to the above-obtained compound (IV) (wherein $R^2$ is hydrogen). Alternatively, the compound (V) in which Q is a protecting group may be prepared by introducing the protecting group into the compound (I-a) (wherein $R^2$ is hydrogen). For example, the compound (V) in which Q is tert.-butoxycarbonyl may be prepared by reacting the compound (I-a) (wherein $R^2$ is hydrogen) with 2-tert.-butoxycarbonylthio-4,6-dimethylpyrimidine, tert.-butoxycarbonyl chloride, tert.-butoxycarbonyl azide or tert.-butoxycarbonyl hydrazide in a solvent (e.g., dioxane, tetrahydrofuran, benzene) at a temperature of 0° to 50° C., especially 10° to 25° C.

Examples of the reactive derivative of the compound (VI) include lower alkanoic acid anhydride (e.g., acetic anhydride, propionic anhydride, butyric anhydride), lower alkanoyl halide (e.g., acetyl chloride, propionyl chloride, butyryl chloride, valeryl chloride,) and benzoyl halide (e.g., benzoyl chloride). The condensation of the compound (V) or a salt thereof with such reactive derivative of the compound (VI) may be carried out in a solvent in the presence or absence of an acid acceptor. The acid acceptor includes, for example, pyridine, triethylamine, N-methylpiperidine, N-methylmorpholine, N-methylpyrrolidine and N-ethyl-N,N-diisopropylamine. Pyridine, benzene, dioxane, tetrahydrofuran, toluene, methylene chloride and acetic acid are suitable as the solvent. When excess amount of acetic anhydride is used as the reactive derivative of the compound (VI), it is not always necessary to use a solvent because said acetic anhydride serves as the solvent. It is preferred to carry out the reaction at a temperature of 20° to 130° C. if the lower alkanoic acid anhydride is used as the reactive derivative of the compound (VI); or at a temperature of 20° to 60° C. if the lower alkanoyl halide or benzoyl halide is used as the reactive derivative.

On the other hand, when the compound (VI) is used in the form of free acid, the condensation thereof with the compound (V) or a salt thereof may be carried out in the presence of a condensing agent in a solvent. The condensing agent includes, for example, dicyclohexylcarbodiimide, N,N'-carbonyl-diimidazole, 1-methyl-2-halopyridinium iodide (e.g., 1-methyl-2-bromopyridinium iodide), methoxyacetylene and $(C_6H_5)_3P—CCl_4$. Methylene chloride, 1,2-dichloroethane, chloroform, benzene, toluene, tetrahydrofuran and dioxane are suitable as the solvent. It is preferred to carry out the reaction at a temperature of 0° to 80° C., especially at 10° to 40° C.

Removal of the protecting group from the compound (VII) may be carried out in the same manner as employed in the method (A).

According to the method (C), the compound (I-c) may be prepared by deacylating the compound (VII) or a salt thereof to give the compound (V) and, when Q is a protecting group, further removing said protecting group from the compound (V).

Deacylation of the compound (VII) or a salt thereof may be carried out by treating said compound with an alkali agent or an acid in a solvent. Examples of the alkali agent include alkali metal hydroxide (e.g., sodium hydroxide, potassium hydroxide) and alkali metal carbonate (e.g., sodium carbonate, potassium carbonate). On the other hand, the acid includes, for example, hydrochloric acid and hydrobromic acid. Alkanol (e.g., methanol, ethanol) and a mixture of said alkanol and water are suitable as the solvent. It is preferred to carry out the reaction at a temperature of 0° to 100° C., especially at 10° to 50° C., if the alkali agent is used; or at a temperature of 0° to 100° C., especially at 20° to 60° C., if the acid is used.

Removal of the protecting group from the compund (V) may be carried out in the same manner as employed in the method (A).

According to the method (D), the compound (I-d) may be prepared by dealkylating the compound (VIII) or a salt thereof. Dealkylation of the compound (VIII) or a salt thereof is conducted by treating it with boron trihalide (e.g., boron tribromide) in a solvent. Methylene chloride, chloroform, 1,2-dichloroethane and chlorobenzene are suitable as the solvent. It is preferred to carry out the reaction at a temperature of −50° to 25° C., especially at −10° to 25° C.

According to the method (E), the compound (I-e) may be prepared by debenzylating the compound (IX) or a salt thereof to give the compound (X) and, when Q is a protecting group, further removing said protecting group from the compound (X).

The removal of the benzyl group from the compound (IX) may be conducted by conventional manners such as, for example, an acid treatment. The acid treatment is accomplished, for example, by reacting said compound with hydrogen bromide in a solvent. Acetic acid, methylene chloride, benzene, ethyl acetate or a mixture thereof are suitable as the solvent. It is preferred to carry out the reaction at a temperature of −10° to 40° C., especially at 0° to 20° C.

Concomitantly, when Q is a protecting group which can be removed by an acid treatment (e.g., benzyloxycarbonyl, p-methoxybenzyloxycarbonyl, tert.-butoxycarbonyl), said protecting group may be removed simultaneously by this reaction. Removal of the other protecting group from the compound (X) may be carried out in the same manner as employed in the Method (A).

The starting compound (II), (V), (VII), (VIII) or (IX) of the invention involves four optical isomers due to the two asymmetric carbon atoms at the 2- and 3-positions of benzothiazepine skeleton. However, since all of the above-mentioned reactions of the invention can be carried out without racemization, the compound (I) of the invention in an optically active form can be readily obtained by the use of an optically active isomer of the compound (II), (V), (VII), (VIII) or (IX) as the starting compound.

Moreover, the starting compound (II) in which $R^2$ is hydrogen may be prepared, for example, according to the method described in Chem. Pharm. Bull., 18, 2028–2037 (1970) or the method shown in the following reaction scheme:

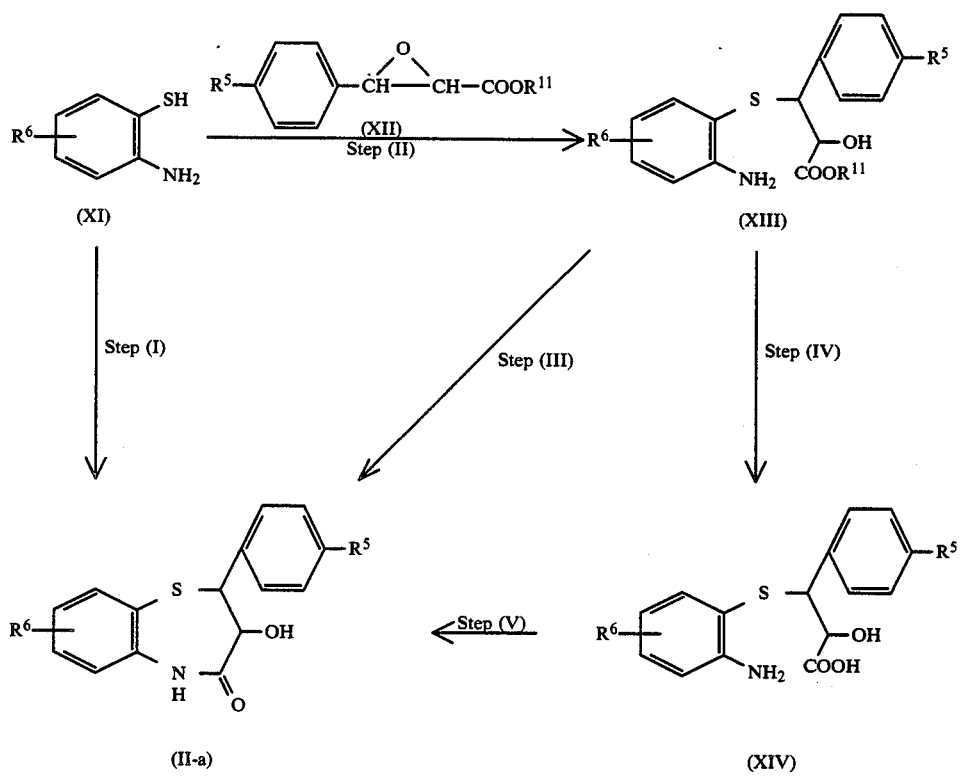

wherein $R^{11}$ is a lower alkyl and $R^5$ and $R^6$ are the same as defined above.

Step (I) in the above-mentioned reaction scheme may be accomplished by heating a mixture of the compounds (XI) and (XII) at 150° to 165° C. either in a solvent (e.g., xylene, diphenyl ether, p-cymene) or without solvent. It is preferred to carry it out in an inert gas (e.g., argon, nitrogen). When the reaction product thus obtained is a mixture of the compound (II-a) and the compound (XIII) or a mixture of two stereoisomers (i.e., cis and trans isomers) of the compound (II-a), they may be separated from each other by their difference in solubility in a solvent (e.g., ethanol, ethyl acetate) or by column chromatography.

The reaction of the compound (XI) with the compound (XII), i.e., Step (II), is accomplished by heating a mixture of the compounds (XI) and (XII) in a solvent (e.g., toluene, acetonitrile, benzene, dioxane, xylene) or without solvent. It is preferred to carry out the reaction at a temperature of 20° to 110° C.

The subsequent optional hydrolysis of the compound (XIII), i.e., Step (IV), is conducted by treating it with an alkali metal hydroxide (e.g., potassium hydroxide, sodium hydroxide) or alkali metal carbonate (e.g., potassium carbonate, sodium carbonate) at 0° to 100° C. in a solvent (e.g., alkanol such as methanol or ethanol, or a mixture of water and said alkanol). If required, the compound (XIV) thus obtained may be resolved into each optical isomers by using a resolving agent such as optically active p-hydroxyphenylglycine esters.

The intramolecular cyclization of the thus-obtained racemic or optically active compound (XIII) or (XIV), i.e., Step (III) or (V), is carried out by heating at 110° to 160° C. either in a solvent (e.g., xylene, toluene, diphenyl ether, p-cymene, acetic acid) or without solvent. The intramolecular cyclization of the compound (XIII) may also be carried out at 0° to 50° C. in the presence of methylsulfinylcarbanion ($CH_3SOCH_2^-$) (prepared from dimethylsulfoxide and sodium hydride) in dimethylsulfoxide.

On the other hand, the compound (II) in which $R^2$ is lower alkanoyl or benzoyl may be prepared by acylating the compound (II-a) with a compound of the formula: $R^7COOH$ (wherein $R^7$ is the same as defined above) or a reactive derivative thereof under the same conitions as employed in the first step of the method (B).

All of the aforementioned reactions can be carried out without racemization.

The compound (I) of the invention can be used for pharmaceutical use either as the free base or a pharmaceutically acceptable acid addition salt thereof. Pharmaceutically acceptable acid addition salts of the compound (I) are, for example, inorganic acid addition salts such as hydrochloride, hydrobromide, hydroiodide, perchlorate, sulfate or phosphate, organic acid addition salts such as oxalate, maleate, fumarate, 2-(p-hydroxybenzoyl)benzoate, succinate or methanesulfonate, and so forth. These salts may be prepared, for example, by neutralizing the compound (I) with an acid. The compound (I) or a pharmaceutically acceptable acid addition salt thereof can be administered either orally or parenterally. Further, the compound (I) or its salt may be used in the form of a pharmaceutical preparation containing the same compound in conjunction or admixture with a pharmaceutical excipient suitable for oral or parenteral administration. Suitable excipients include, for example, starch, lactose, glucose, potassium phosphate, corn starch, arabic gum, stearic acid and other known medicinal excipients. The pharmaceutical preparations may be in solid form such as tablets, pills, capsules or suppositories; or in liquid form such as solutions, suspensions or emulsions. Further, when administered parenterally, the pharmaceutical preparation may be used in the form of injections.

As mentioned hereinbefore, the compound (I) of the present invention has a potent platelet aggregation-inhibiting activity and is useful for the treatment, amelioration or prophylaxis of thrombotic diseases such as cerebral infarction (or cerebral thrombosis), transient cerebral ischemia, myocardial infarction (or coronary thrombosis), pulmonary infarction, peripheral vascular embolism, thromboangitis and/or other thromboembolism (e.g., the thromboembolism following heart valve replacement).

Therapeutic dose of the compound (I) or its salt depends on route of administration, the age, weight and conditions of patients, and particular diseases to be treated. In general, however, it may be used at a dose of 0.05 to 50 mg/kg/day, especially at a dose of 0.5 to 20 mg/kg/day in the case of oral administration or at a dose of 0.05 to 10 mg/kg/day in the case of parenteral administration (e.g., intravenous injection).

Practical and presently preferred embodiments of the present invention are illustratively shown in the following lines. Throughout the specification and claims, the terms "lower alkyl", "lower alkylthio", "lower alkoxy", "lower alkanoyl" and "lower alkanoic acid" should be interpreted as referring to straight or branched alkyl of one to 4 carbon atoms, straight or branched alkylthio of one to 4 carbon atoms, straight or branched alkoxy of one to 4 carbon atoms, straight or branched alkanoyl of 2 to 5 carbon atoms and straight or branched alkanoic acid of 2 to 5 carbon atoms, respectively. Concomitantly, throughout the specification and claims, the term "threo" means that the hydroxy and substituted-phenylthio groups substituted at the 2- and 3-positions of propionic acid have threo-type configuration (i.e., said two groups are placed on opposite of the central bond in the Fisher's projection formula).

EXPERIMENT 1

(Inhibitory effects in vitro on collagen-induced platelet aggregation of rat or human platelets)
(Method)

Nine volumes of rat or human blood were mixed with one volume of an aqueous 3.8% (w/v) trisodium citrate solution, and the mixture was centrifuged to give platelet-rich plasma ("PRP") as the supernatant solution. The bottom layer was further centrifuged to give platelet-poor plasma ("PPP") as the supernatant solution. Platelet counts were adjusted to about $0.8-1 \times 10^6/mm^3$ for rat PRP and about $4 \times 10^5/mm^3$ for human PRP by dilution with PPP. After a mixture of 200 μl of the diluted PRP and 25 μl of a test compound solution was stirred at 37° C. for 2 minutes, 25 μl of a collagen solution (Biochim. Biophys. Acta, 186, 254 (1969)) were added thereto. The degree of platelet aggregation was examined by Born's method (Nature, 194, 927 (1962)) and the percentage inhibition of platelet aggregation was calculated therefrom.

The inhibitory effect of the test compound on collagen-induced platelet aggregation was estimated in term of $IC_{50}$ (i.e., the concentration of the test compound which was required to induce 50% inhibition of collagen-induced platelet aggregation).

(Results)

The results are shown in Tables 1 and 2.

TABLE 1

| (Platelet aggregation-inhibiting activity on Rat platelets) | |
|---|---|
| Compounds | $IC_{50}$ (μg/ml) |
| (−)-cis-2-(4-methylphenyl)-3-hydroxy-5-[2-(N—methylamino)ethyl]-8-methyl-2,3-dihydro-1,5-benzothiazepin-4(5H)—one hydrochloride | 0.1 |
| (±)-cis-2-(4-methylphenyl)-3-hydroxy-5-[2-(N—methylamino)ethyl]-8-methyl-2,3-dihydro-1,5-benzothiazepin-4(5H)—one sulfate | 0.1–0.3 |
| (±)-cis-2-(4-methylphenyl)-3-acetoxy-5-[2-(N—methylamino)ethyl]-8-methyl-2,3-dihydro-1,5-benzothiazepin-4(5H)—one hydrochloride | 0.5 |
| (±)-cis-2-(4-methylphenyl)-3-hydroxy-5-[2-(N—methylamino)ethyl]-8-methoxy-2,3-dihydro-1,5-benzothiazepin-4(5H)—one hydrochloride | 0.3–1 |

TABLE 1-continued (Platelet aggregation-inhibiting activity on Rat platelets)

| Compounds | $IC_{50}$ ($\mu$g/ml) |
|---|---|
| Acetylsalicylic acid | about 45 |

TABLE 2

(Platelet aggregation-inhibiting activity on Human platelets)

| Compounds | $IC_{50}$ ($\mu$g/ml) |
|---|---|
| (−)-cis-2-(4-methylphenyl)-3-hydroxy-5-[2-(N—methylamino)ethyl]-8-methyl-2,3-dihydro-1,5-benzothiazepin-4(5H)—one hydrochloride | 0.003–0.03 |
| (±)-cis-2-(4-methylphenyl)-3-hydroxy-5-[2-(N—methylamino)ethyl]-8-methyl-2,3-dihydro-1,5-benzothiazepin-4(5H)—one hydrochloride | 0.3 |
| (±)-cis-2-(4-methylphenyl)-3-hydroxy-5-[2-(N—methylamino)ethyl]-8-methyl-2,3-dihydro-1,5-benzothiazepin-4(5H)—one sulfate | 0.3 |
| (±)-cis-2-(4-methylphenyl)-3-acetoxy-5-[2-(N—methylamino)ethyl]-8-methoxy-2,3-dihydro-1,5-benzothiazepin-4(5H)—one oxalate | 0.5 |
| (±)-cis-2-(4-methylphenyl)-3-hydroxy-5-[2-(N—methylamino)ethyl]-8-methoxy-2,3-dihydro-1,5-benzothiazepin-4(5H)—one hydrochloride | 0.5 |
| (±)-cis-2-(4-methylphenyl)-3-hydroxy-5-[2-(N—methylamino)ethyl]-2,3-dihydro-1,5-benzothiazepin-4(5H)—one hydrobromide | 0.3 |
| Acetylsalicylic acid | about 20 |

EXPERIMENT 2

(Inhibitory effect ex vivo on collagen-induced platelet aggregation of rat platelets)

(Method)

A test compound solution (Dose: 10 mg/kg) was orally administered to Sprague-Dawley rats fasted for about 20 hours. Three hours after administration, blood was collected from the abdominal aorta of the rats. Nine volumes of the blood were mixed with one volume of an aqueous 3.8% (w/v) trisodium citrate solution, and the mixture was centrifuged to give platelet-rich plasma ("PRP") as the supernatant solution. The bottom layer was further centrifuged to give platelet-poor plasma ("PPP") as the supernatant solution. PRP was diluted with PPP so that the blood platelet counts were $0.8-1 \times 10^6/\text{mm}^3$. 25 $\mu$l of a collagen solution (Biochim. Biophys. Acta., 186, 254 (1969)) were added to 225 $\mu$l of the diluted PRP to induce platelet aggregation. The degree of platelet aggregation was examined by Born's method (Nature., 194, 927 (1962)) and the percentage inhibition of platelet aggregation was calculated therefrom. The inhibitory effect of the test compound on collagen-induced platelet aggregation was estimated in terms of (−) if the percentage inhibition is less than 25%, (+) if the percentage inhibition is not less than 25% but less than 50%, and (++) if the percentage inhibition is not less than 50%.

(Results)

The results are shown in Table 3.

TABLE 3

| Compounds | Platelet aggregation inhibiting activity |
|---|---|
| (±)-cis-2-(4-methoxyphenyl)-3-acetoxy-5-[2-(N—methylamino)ethyl]-8-methyl-2,3-dihydro-1,5-benzothiazepin-4(5H)—one hydrochloride | ++ |
| (−)-cis-2-(4-methoxyphenyl)-3-acetoxy-5-[2-(N—methylamino)ethyl]-8-methyl-2,3-dihydro-1,5-benzothiazepin-4(5H)—one oxalate | ++ |
| (±)-cis-2-(4-methylphenyl)-3-acetoxy-5-[2-(N—methylamino)ethyl]-8-methyl-2,3-dihydro-1,5-benzothiazepin-4(5H)—one hydrochloride | ++ |
| (±)-cis-2-(4-methylphenyl)-3-hydroxy-5-[2-(N—methylamino)ethyl]-8-methyl-2,3-dihydro-1,5-benzothiazepin-4(5H)—one hydrochloride | ++ |
| (±)-cis-2-(4-methoxyphenyl)-3-hydroxy-5-[2-(N—methylamino)ethyl]-8-methyl-2,3-dihydro-1,5-benzothiazepin-4(5H)—one hydrochloride | ++ |
| (−)-cis-2-(4-methoxyphenyl)-3-hydroxy-5-[2-(N—methylamino)ethyl]-8-methyl-2,3-dihydro-1,5-benzothiazepin-4(5H)—one hydrobromide | ++ |
| (±)-cis-2-(4-methoxyphenyl)-3,8-dihydroxy-5-[2-(N—methylamino)ethyl]-2,3-dihydro-1,5-benzothiazepin-4(5H)—one hydrochloride | ++ |

EXAMPLE 1

(1) A mixture of 2 g of (±)-cis-2-(4-methoxyphenyl)-3-hydroxy- 8-methyl-2,3-dihydro-1,5-benzothiazepin-4(5H)-one, 0.42 g of powdered potassium hydroxide and 15 ml of dimethylsulfoxide is stirred at 50° C. for 30 minutes. A solution of 2.64 g of 2-(N-benzyloxycarbonyl-N-methylamino)ethyl chloride in 5 ml of dimethylsulfoxide is added to the mixture, and the mixture is stirred at 50° C. for 3 days. The mixture is poured into ice-water, and the aqueous mixture is extracted with ethyl acetate. The extract is washed with a saturated sodium chloride solution, dried and evaporated under reduced pressure to remove solvent. The residue is purified by silica gel chromatography (solvent, chloroform: ethyl acetate=10:1). 2.95 g of (+)-cis-2-(4-methoxyphenyl)-3-hydroxy-5-[2-(N-benzyloxycarbonyl-N-methylamino)ethyl]-8-methyl-2,3-dihydro-1,5-benzothiazepin-4(5H)-one are obtained as an oil.

(2) A mixture of 2.49 g of (±)-cis-2-(4-methoxyphenyl)-3-hydroxy-5-[2-(N-benzyloxycarbonyl-N-methylamino)ethyl]-8-methyl-2,3-dihydro-1,5-benzothiazepin-4(5H)-one, 15 ml of acetic anhydride and 5 ml of pyridine is stirred at 100° C. for 2 hours. The mixture is evaporated under reduced pressure to remove acetic anhydride and pyridine. Toluene is added to the residue, and the mixture is evaporated under reduced pressure to remove solvent (This operation is repeated again). 3.08 g of (±)-cis-2-(4-methoxyphenyl)-3-acetoxy-5-[2-(N-benzyloxycarbonyl-N-methylamino)ethyl]-8-methyl-2,3-dihydro-1,5-benzothiazepin-4(5H)-one are obtained as an oil.

(3) A mixture of 3.08 g of (±)-cis-2-(4-methoxyphenyl)- 3-acetoxy-5-[2-(N-benzyloxycarbonyl-N-methylamino)ethyl]-8-methyl-2,3-dihydro-1,5-benzothiazepin-4(5H)-one, 10 ml of acetic acid and 5 ml of 25% hydrogen bromide-acetic acid is stirred at room temperature for 2 hours. The mixture is evaporated under reduced pressure to remove solvent. Toluene is added to the residue, and crystalline precipitates are collected by filtration and washed with ether. The crude product (hydrobromide) is converted to its free base, and the resultant free base is converted to its hydrochloride and then recrystallized from ethanol. 1.2 g of (±)-cis-2-(4-methoxyphenyl)-3-acetoxy-5-[2-(N-methylamino)ethyl]-8-methyl-2,3-dihydro-1,5-benzothiazepin-4(5H)-one hydrochloride. $\frac{1}{2}H_2O.\frac{1}{2}C_2H_5OH$ are obtained.

M.p. 154°–156° C.

EXAMPLES 2 TO 8

The following compounds are obtained from the corresponding 3-hydroxy-5-unsubstituted compounds in the same manner as described in Example 1-(1), (2) and (3).

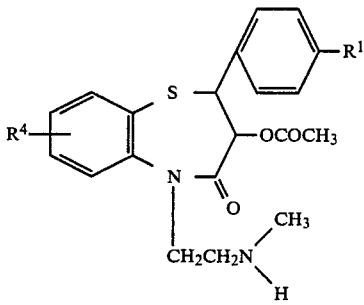

| Example Nos. | R[1] | R[4] | Optical isomer | M.p., etc. |
|---|---|---|---|---|
| 2. | CH₃ | 8-CH₃ | ± | hydrochloride, M.p. 200–202° C. (recrystallized from isopropanol-ether) |
| 3. | CH₃ | 8-CH₃ | ± | oxalate, M.p. 140–142° C. (decomp.) (recrystallized from ethanol) |
| 4. | CH₃ | 8-OCH₃ | ± | oxalate hemihydrate, M.p. 143–147° C. (recrystallized from ethanol) |
| 5. | OCH₃ | 6-OCH₃ | ± | oxalate hemihydrate, M.p. 53–56° C. (recrystallized from ethanol) |
| 6. | CH₃ | 8-F | ± | oxalate, M.p. 190–191.5° C. (decomp.) (recrystallized from dimethylformamide-ethanol) |
| 7. | CH₃ | 7-CH₃ | ± | oxalate, M.p. 200.5–203° C. (decomp.) (recrystallized from dimethylformamide-ethanol) |
| 8. | OCH₃ | 8-F | ± | oxalate, M.p. 165–167° C. (recrystallized from dimethylformamide-ethanol) |

Note:
The compounds listed in the Table are all cis isomers.

EXAMPLE 9

(1) A mixture of 6.3 g of (−)-cis-2-(4-methoxyphenyl)-3-hydroxy-8-methyl-2,3-dihydro-1,5-benzothiazepin-4(5H)-one, 4.65 g of 2-(N-benzyl-N-methylamino)ethyl chloride hydrochloride, 7.2 g of potassium carbonate and 80 ml of acetone is refluxed for 20 hours. Insoluble materials are removed by filtration, and the filtrate is evaporated under reduced pressure to remove solvent. The residue is converted to its perchlorate and recrystallized from methanol. 10.8 g of (−)-cis-2-(4-methoxyphenyl)-3-hydroxy-5-[2-(N-benzyl-N-methylamino)ethyl]-8-methyl-2,3-dihydro-1,5-benzothiazepin-4(5H)-one perchlorate are obtained.
M.p. 178°–181° C.
$[\alpha]_D^{20}$ −86.1° (C=0.18, methanol).

(2) 10.7 g of (−)-cis-2-(4-methoxyphenyl)-3-hydroxy-5-[2-(N-benzyl-N-methylamino)ethyl]-8-methyl-2,3-dihydro-1,5-benzothiazepin-4(5H)-one perchlorate is converted to its free base, and 80 ml of acetic anhydride and one ml of pyridine are added thereto. The mixture is heated at 100° C. for 4 hours. The mixture is evaporated under reduced pressure to remove acetic anhydride and pyridine. Benzene is added to the residue, and the mixture is evaporated under reduced pressure to remove solvent. 10.37 g of (−)-cis-2-(4-methoxyphenyl)-3-acetoxy-5-[2-(N-benzyl-N-methylamino)ethyl]-8-methyl-2,3-dihydro-1,5-benzothiazepin-4(5H)-one are obtained as an oil.

(3) A mixture of 10.37 g of (−)-cis-2-(4-methoxyphenyl)-3-acetoxy-5-[2-(N-benzyl-N-methylamino)ethyl]-8-methyl-2,3-dihydro-1,5-benzothiazepin-4(5H)-one and 125 ml of benzene is refluxed. A solution of 9 g of benzyloxycarbonyl chloride in 25 ml of benzene is added dropwise to the mixture for 30 minutes, and the mixture is refluxed for 4 hours. Then, the mixture is evaporated under reduced pressure to remove solvent. 11.8 g of (−)-cis-2-(4-methoxyphenyl)-3-acetoxy-5-[2-(N-benzyloxycarbonyl-N-methylamino)ethyl]-8-methyl-2,3-dihydro-1,5-benzothiazepin-4(5H)-one are obtained as an oil.

(4) A mixture of 11.8 g of (−)-cis-2-(4-methoxyphenyl)-3-acetoxy-5-[2-(N-benzyloxycarbonyl-N-methylamino)ethyl]-8-methyl-2,3-dihydro-1,5-benzothiazepin-4(5H)-one, 25 ml of 25% hydrogen bromide-acetic acid and 50 ml of acetic acid is stirred at room temperature for 2 hours. 800 ml of anhydrous ether are added to the mixture. The resultant amorphous powder is collected by decantation and dissolved in acetone. The solution is diluted with ether, and the resultant amorphous powder is collected by decantation and dissolved in water. The solution is alkalized with an aqueous ammonium hydroxide solution, and then extracted with chloroform. The extract is washed with water, dried and then evaporated under reduced pressure to remove solvent. The residue is converted to its oxalate and recrystallized from ethanol. 8.4 g of (−)-cis-2-(4-methoxyphenyl)-3-acetoxy-5-[2-(N-methylamino)ethyl]-8-methyl-2,3-dihydro-1,5-benzothiazepin-4(5H)-one oxalate are obtained.
M.p. 166°–168° C.
$[\alpha]_D^{20}$ −79.4° (C=0.36 methanol).

EXAMPLES 10 to 14

(1) The following compounds are obtained from the corresponding N-unsubstituted compounds in the same manner as described in Example 9-(1).

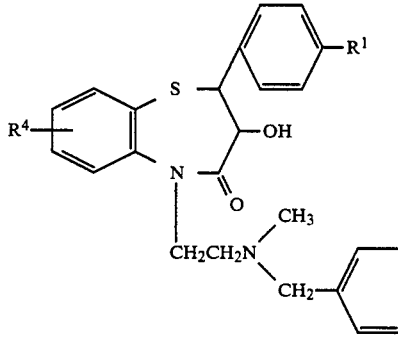

| R[1] | R[4] | Optical isomer | M.p., etc. |
|---|---|---|---|
| OCH₃ | 8-CH₃ | + | perchlorate, M.p. 175–177° C. (recrystallized from methanol) $[\alpha]_D^{20}$ 85.8° (C = 0.17, methanol) |
| CH₃ | 8-CH₃ | ± | hydrobromide hemihydrate, M.p. 177–182° C. (recrystallized methanol-ether) |
| OCH₃ | 8-SCH₃ | ± | oil |
| OCH₃ | 7-SCH₃ | ± | oil |

-continued

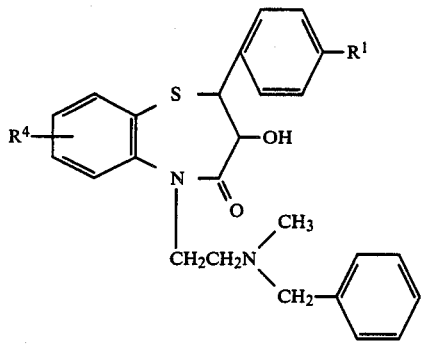

| R¹ | R⁴ | Optical isomer | M.p., etc. |
|---|---|---|---|
| OCH₃ | 9-F | ± | oil |

Note:
The compounds listed in the Table are all cis isomers.

(2) The compounds obtained in paragraph (1) are treated in the same manner as described in Example 9-(2), (3) and (4), whereby the following compounds are obtained, respectively.

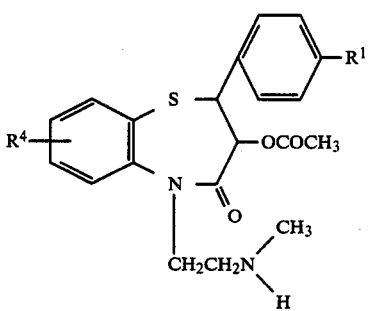

| Example Nos. | R¹ | R⁴ | Optical isomer | M.p., etc. |
|---|---|---|---|---|
| 10. | OCH₃ | 8-CH₃ | + | oxalate, M.p. 166–168° C. (recrystallized from ethanol) $[\alpha]_D^{20}$ + 80.2° (C = 0.35, methanol) |
| 11. | CH₃ | 8-CH₃ | ± | hydrochloride, M.p. 200–202° C. (recrystallized from isopropanol-ether) |
| 12. | OCH₃ | 8-SCH₃ | ± | hydrobromide-isopropanol, M.p. 148–150° C., (recrystallized from isopropanol) |
| 13. | OCH₃ | 7-SCH₃ | ± | hydrobromide-isopropanol, M.p. 122–124° C. (recrystallized from isopropanol) |
| 14. | OCH₃ | 9-F | ± | hydrobromide, M.p. 193–196° C. (recrystallized from isopropanol) |

Note:
The compounds listed in the Table are all cis isomer.

EXAMPLE 15

(1) A mixture of 5.96 g of (±)-cis-2-(4-methylphenyl)-3-hydroxy-8-methyl-2,3-dihydro-1,5-benzothiazepin-4(5H)-one, 5.89 g of 2-(N-benzyloxycarbonyl-N-methylamino)ethyl chloride, 1.68 g of potassium hydroxide and 85 ml of dimethylsulfoxide is treated in the same manner as described in Example 1-(1). The crude product thus obtained is purified by silica gel chromatography (solvent, benzene:ethyl acetate=9:1). 7.89 g of (±)-cis-2-(4-methylphenyl)-3-hydroxy-5-[2-(N-benzyloxycarbonyl-N-methylamino)ethyl]-8-methyl-2,3-dihydro-1,5-benzothiazepin-4(5H)-one are obtained as an oil.

(2) A mixture of 1.6 g of (±)-cis-2-(4-methylphenyl)-3-hydroxy-5-[2-(N-benzyloxycarbonyl-N-methylamino)ethyl]-8-methyl-2,3-dihydro-1,5-benzothiazepin-4(5H)-one, 0.69 g of benzoyl chloride, 5 ml of pyridine and 2 ml of benzene is stirred at room temperature for 2 hours. The mixture is poured into ice-water, and the aqueous mixture is extracted with ethyl acetate. The extract is washed with water, dried and then evaporated under reduced pressure to remove solvent. 2.14 g of (±)-cis-2-(4-methylphenyl)-3-benzoyloxy-5-[2-(N-benzyloxycarbonyl-N-methylamino)ethyl]-8-methyl-2,3-dihydro-1,5-benzothiazepin-4(5H)-one are obtained as an oil.

(3) A mixture of 2.14 g of (±)-cis-2-(4-methylphenyl)-3-benzoyloxy-5-[2-(N-benzyloxycarbonyl-N-methylamino)ethyl]-8-methyl-2,3-dihydro-1,5-benzothiazepin-4(5H)-one, 2 ml of 25% hydrogen bromide-acetic acid and 2 ml of acetic acid is stirred at room temperature for 2 hours. Ether is added to the mixture, and the resultant crystals are collected by decantation. After the crystals are thoroughly washed with ether, water is added thereto. The mixture is alkalized with an aqueous ammonium hydroxide solution, and then extracted with ethyl acetate. The extract is washed with water, dried and evaporated under reduced pressure to remove solvent. The residue is converted to its oxalate and recrystallized from a mixture of dimethylformamide and ethanol. 0.85 g of (±)-cis-2-(4-methylphenyl)-3-benzoyloxy-5-[2-(N-methylamino)ethyl]-8-methyl-2,3-dihydro-1,5-benzothiazepin-4(5H)-one oxalate is obtained.

M.p. 212°–213.5° C.

EXAMPLE 16

A mixture of 1.38 g of (±)-cis-2-(4-methylphenyl)-3-hydroxy-5-[2-(N-benzyloxycarbonyl-N-methylamino)ethyl]-8-methyl-2,3-dihydro-1,5-benzothiazepin-4(5H)-one, 0.45 g of isobutyryl chloride, 5 ml of pyridine and 2 ml of benzene is treated in the same manner as described in Example 15-(2). The product, i.e., (±)-cis-2-(4-methylphenyl)-3-isobutyryloxy-5-[2-(N-benzyloxycarbonyl-N-methylamino)ethyl]-8-methyl-2,3-dihydro-1,5-benzothiazepin-4(5H)-one, is treated in the same manner as described in Example 15-(3). 0.40 g of (±)-cis-2-(4-methylphenyl)-3-isobutyryloxy-5-[2-(N-methylamino)ethyl]-8-methyl-2,3-dihydro-1,5-benzothiazepin-4(5H)-one oxalate is obtained.

M.p. 188.5°–190.5° C. (decomp.).

EXAMPLE 17

A mixture of 1.35 g of (±)-cis-2-(4-methylphenyl)-3-hydroxy-5-[2-(N-benzyloxycarbonyl-N-methylamino)ethyl]-8-methyl-2,3-dihydro-1,5-benzothiazepin-4(5H)-one, 0.44 g of n-butyryl chloride, 5 ml of pyridine and 2 ml of benzene is treated in the same manner as described in Example 15-(2). The product, i.e., (±)-cis-2-(4-methylphenyl)-3-n-butyryloxy-5-[2-(N-benzyloxycarbonyl-N-methylamino)ethyl]-8-methyl-2,3-dihydro-1,5-benzothiazepin-4(5H)-one, is treated in the same manner as described in Example 15-(3). 0.43 g of (±)-cis-2-(4-methylphenyl)-3-n-butyryloxy-5-[2-(N-methylamino)ethyl ]-8-methyl-2,3-dihydro-1,5-benzothiazepin-4(5H)-one oxalate is obtained.

M.p. 185.5°–186° C.

EXAMPLE 18

A mixture of 1.46 g of (±)-cis-2-(4-methylphenyl)-3-hydroxy-5-[2-(N-benzyloxycarbonyl-N-methylamino)ethyl]-8-methyl-2,3-dihydro-1,5-benzothiazepin-4(5H)-one, 0.42 g of propionyl chloride, 5 ml of pyridine and 2 ml of benzene is treated in the same manner as described in Example 15-(2). The product, i.e., (±)-cis-2-(4-methylphenyl)-3-propionyloxy-5-[2-(N-benzyloxycarbonyl-N-methylamino)ethyl]-8-methyl-2,3-dihydro-1,5-benzothiazepin-4(5H)-one, is treated in the same manner as described in Example 15-(3). 0.45 g of (±)-cis-2-(4-methylphenyl)-3-propionyloxy-5-[2-(N-methylamino)ethyl]-8-methyl-2,3-dihydro-1,5-benzothiazepin-4(5H)-one hemioxalate is obtained.

M.p. 128°–132° C.

EXAMPLE 19

(1) A mixture of 5 g of (±)-cis-2-(4-methoxyphenyl)-3-hydroxy-8-benzyloxy-2,3-dihydro-1,5-benzothiazepin-4(5H)-one, 3.8 g of 2-(N-benzyloxycarbonyl-N-methylamino)ethyl chloride, 1.1 g of potassium hydroxide and 70 ml of dimethylsulfoxide is treated in the same manner as described in Example 1-(1). 3.75 g of (±)-cis-2-(4-methoxyphenyl)-3-hydroxy-5-[2-(N-benzyloxycarbonyl-N-methylamino)ethyl]-8-benzyloxy-2,3-dihydro-1,5-benzothiazepin-4(5H)-one are obtained as an oil.

(2) A mixture of 3.75 g of (±)-cis-2-(4-methoxyphenyl)-3-hydroxy-5-[2-(N-benzyloxycarbonyl-N-methylamino)ethyl]-8-benzyloxy-2,3-dihydro-1,5-benzothiazepin-4(5H)-one, 23 ml of acetic anhydride and 8 ml of pyridine is treated in the same manner as described in Example 1-(2). 4.18 g of (±)-cis-2-(4-methoxyphenyl)-3-acetoxy-5-[2-(N-benzyloxycarbonyl-N-methylamino)ethyl]-8-benzyloxy-2,3-dihydro-1,5-benzothiazepin-4(5H)-one are obtained as an oil.

(3) A mixture of 2.31 g of (±)-cis-2-(4-methoxyphenyl)-3-acetoxy-5-[2-(N-benzyloxycarbonyl-N-methylamino)ethyl]-8-benzyloxy-2,3-dihydro-1,5-benzothiazepin-4(5H)-one, 3.5 ml of 25% hydrogen bromide-acetic acid and 7 ml of acetic acid is stirred at room temperature for one hour. Ether is added to the mixture, and crystalline precipitates are collected by filtration and washed with ether. The crystals are suspended in water, and an aqueous sodium bicarbonate solution is added to the suspension. The mixture is extracted with chloroform (the aqueous layer is hereinafter referred to as "Aqueous Layer"), and the extract is washed with water, dried and then evaporated under reduced pressure to remove solvent. The residue is purified by silica gel chromatography (solvent, chloroform:ethanol=9:1). The resultant oil (0.29 g) is converted to its hydrochloride and recrystallized from a mixture of ethanol and ether. 0.21 g of (±)-cis-2-(4-methoxyphenyl)-3-acetoxy-5-[2-(N-methylamino)ethyl]-8-benzyloxy-2,3-dihydro-1,5-benzothiazepin-4(5H)-one hydrochloride is obtained.

M.p. 175°–178° C.

On the other hand, an aqueous sodium bicarbonate solution is added to the aqueous layer obtained above, and the mixture is extracted with chloroform. The extract is washed with water, dried and evaporated under reduced pressure to remove solvent. The residue is converted to its hydrochloride and recrystallized from ethanol. 0.22 g of (±)-cis-2-(4-methoxyphenyl)-3-acetoxy-5-[2-(N-methylamino)ethyl]-8-hydroxy-2,3-dihydro-1,5-benzothiazepin-4(5H)-one hydrochloride hemihydrate is obtained.

M.p. 242°–245° C. (decomp.).

EXAMPLE 20

A mixture of 1.97 g of (±)-cis-2-(4-methoxyphenyl)-3-acetoxy-5-[2-(N-benzyloxycarbonyl-N-methylamino)ethyl]-8-benzyloxy-2,3-dihydro-1,5-benzothiazepin-4(5H)-one, 3.6 ml of 25% hydrogen bromide-acetic acid and 7 ml of acetic acid is stirred at room temperature for 3 hours. Ether is added to the mixture, and crystalline precipitates are collected by filtration and washed with ether. The crystals are dissolved in water, and the solution is alkalized with an aqueous ammonium hydroxide solution. The mixture is extracted with chloroform, and the extract is washed with water, dried and evaporated under reduced pressure to remove solvent. The residue is purified by silica gel chromatography (solvent, chloroform:ethanol=9:1). The resultant oil (0.58 g) is converted to its hydrochloride and recrystallized from ethanol. 0.54 g of (±)-cis-2-(4-methoxyphenyl)-3-acetoxy-5-[2-(N-methylamino)ethyl]-8-hydroxy-2,3-dihydro-1,5-benzothiazepin-4(5H)-one hydrochloride is obtained. The physicochemical properties of the product are identical with those of the product obtained in Example 19-(3).

EXAMPLE 21

A mixture of 1.1 g of (±)-cis-2-(4-methoxyphenyl)-3-acetoxy-5-[2-(N-methylamino)ethyl]-8-methyl-2,3-dihydro-1,5-benzothiazepin-4(5H)-one hydrobromide, 10 ml of an aqueous 5% sodium hydroxide solution and 5 ml of ethanol is stirred at room temperature for 3 hours. Water is added to the mixture, and the aqueous mixture is extracted with ethyl acetate. The extract is washed with an aqueous sodium chloride solution, dried and evaporated under reduced pressure to remove solvent. The residue is converted to its hydrochloride and recrystallized from ethanol. 0.46 g of (±)-cis-2-(4-methoxyphenyl)-3-hydroxy-5-[2-(N-methylamino)ethyl]-8-methyl-2,3-dihydro-1,5-benzothiazepin-4(5H)-one hydrochloride is obtained.

M.p. 230°–232° C. (decomp.).

EXAMPLES 22 to 31

The following compounds are obtained from the corresponding 3-acetoxy compounds in the same manner as described in Example 21.

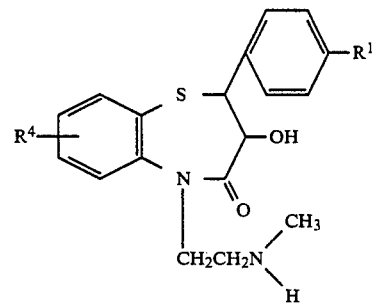

| Example Nos. | R¹ | R⁴ | Optical isomer | M.p., etc. |
|---|---|---|---|---|
| 22. | CH₃ | 8-CH₃ | ± | hydrochloride, M.p. 238–243° C. (decomp.) (recrystallized from |

-continued

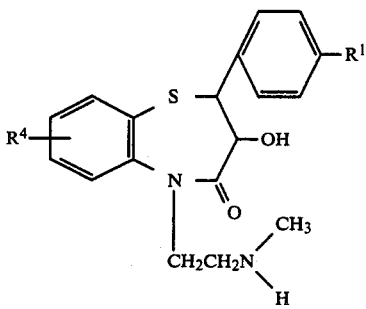

| Example Nos. | R¹ | R⁴ | Optical isomer | M.p., etc. |
|---|---|---|---|---|
| | | | | dimethylformamide) |
| 23. | CH₃ | 8-CH₃ | ± | sulfate hydrate, M.p. 130–131° C. (recrystallized from ethanol) |
| 24. | OCH₃ | 8-CH₃ | + | hydrobromide, M.p. 130–133° C. (recrystallized from ethanol) $[\alpha]_D^{20} + 86.5°$ (C = 0.39, methanol) |
| 25. | OCH₃ | 8-CH₃ | − | hydrobromide, M.p. 131–135° C. (recrystallized from ethanol) $[\alpha]_D^{20} - 86.3°$ (C = 0.28, methanol) |
| 26. | CH₃ | 8-OCH₃ | ± | hydrochloride, M.p. 228–231° C. (recrystallized from ethanol) |
| 27. | OCH₃ | 8-OH | ± | hydrochloride, M.p. 235–238° C. (decomp.) (recrystallized from dimethylformamide-ethanol) |
| 28. | OCH₃ | 9-F | ± | hydrochloride hemihydrate, M.p. 144–147° C. (recrystallized from isopropanol) |
| 29. | OCH₃ | 8-SCH₃ | ± | hydrochloride, M.p. 220–225° C. (decomp.) (recrystallized from dimethylformamide-ethanol) |
| 30. | OCH₃ | 7-SCH₃ | ± | hydrochloride, M.p. 177–180° C. (decomp.) (recrystallized from ethanol) |
| 31. | CH₃ | 7-CH₃ | ± | hydrobromide hemihydrate, M.p. 243–245° C. (decomp.) (recrystallized from ethanol-ether) |

Note:
The compounds listed in the Table are all cis isomers.

EXAMPLE 32

(1) A mixture of 0.90 g of (−)-cis-2-(4-methylphenyl)-3-hydroxy-8-methyl-2,3-dihydro-1,5-benzothiazepin-4(5H)-one, 1.03 g of 2-(N-benzyloxycarbonyl-N-methylamino)ethyl chloride, 0.20 g of potassium hydroxide and 10 ml of dimethylsulfoxide is treated in the same manner as described in Example 1-(1), whereby 0.62 g of (−)-cis-2-(4-methylphenyl)-3-hydroxy-5-[2-(N-benzyloxycarbonyl-N-methylamino)ethyl]-8-methyl-2,3-dihydro-1,5-benzothiazepin-4(5H)-one is obtained as an oil.

(2) A mixture of 0.73 g of (−)-cis-2-(4-methylphenyl)-3-hydroxy-5-[2-(N-benzyloxycarbonyl-N-methylamino)ethyl]-8-methyl-2,3-dihydro-1,5-benzothiazepin-4(5H)-one, 5 ml of acetic anhydride and 0.1 ml of pyridine is treated in the same manner as described in Example 1-(2), whereby 0.92 g of (−)-cis-2-(4-methylphenyl)-3-acetoxy-5-[2-(N-benzyloxycarbonyl-N-methylamino)ethyl]-8-methyl-2,3-dihydro-1,5-benzothiazepin-4(5H)-one is obtained as an oil. (3) A mixture of 0.92 g of (−)-cis-2-(4-methylphenyl)-3-acetoxy-5-[2-(N-benzyloxycarbonyl-N-methylamino)ethyl]-8-methyl-2,3-dihydro-1,5-benzothiazepin-4(5H)-one, 2 ml of 25% hydrogen bromide-acetic acid and 2 ml of acetic acid is stirred at room temperature for 2 hours. The mixture is evaporated under reduced pressure to remove solvent. Toluene is added to the residue, and the mixture is evaporated under reduced pressure to remove solvent. Ether is added to the residue, and the resultant crystals are collected by filtration and washed with ether. A mixture of the crystals thus obtained, 2 ml of ethanol and 2 ml of an aqueous 5% sodium hydroxide solution is stirred at room temperature for 2 hours. The mixture is adjusted to pH 8 with acetic acid, and then extracted with chloroform. The extract is washed with water, dried and evaporated under reduced pressure to remove solvent. The residue is converted to its hydrochloride and recrystallized from isopropanol. 0.32 g of (−)-cis-2-(4-methylphenyl)-3-hydroxy-5-[2-(N-methylamino)ethyl]-8-methyl-2,3-dihydro-1,5-benzothiazepin-4(5H)-one hydrochloride hemihydrate is obtained.

M.p. 128°–145° C.
$[\alpha]_D^{20} - 103.8°$ (C=0.29, methanol).

EXAMPLE 33

(+)-cis-2-(4-methylphenyl)-3-hydroxy-5-[2-N-methylamino)ethyl]-8-methyl-2,3-dihydro-1,5-benzothiazepin-4(5H)-one hydrochloride hemihydrate is obtained from (+)-cis-2-(4-methylphenyl)-3-hydroxy-8-methyl-2,3-dihydro-1,5-benzothiazepin-4(5H)-one in the same manner as described in Example 32-(1), (2) and (3).

M.p. 130°–147° C. (recrystallized from isopropanol).
$[\alpha]_D^{20} + 103.84°$ (C=0.182, methanol).

EXAMPLE 34

A solution of 6.34 g of boron tribromide in 50 ml of methylene chloride is cooled at −50° C., and a solution of 1.89 g of (−)-cis-2-(4-methoxyphenyl)-3-hydroxy-5-[2-(N-methylamino)ethyl]-8-methyl-2,3-dihydro-1,5-benzothiazepin-4(5H)-one in 50 ml of methylene chloride is added dropwise thereto for 30 minutes. The temperature of the mixture is gradually raised to room temperature, and said mixture is stirred at the same temperature for 30 minutes. The mixture is evaporated under reduced pressure to remove solvent. Chloroform is added to the residue, and the mixture is poured into ice-water. The aqueous mixture is alkalized with an aqueous sodium bicarbonate solution, and the chloroform layer is collected therefrom. The chloroform layer is washed with water, dried and evaporated under reduced pressure to remove solvent. The residue is converted to its 2-(p-hydroxybenzoyl)-benzoate and recrystallized from a mixture of acetone and ether. 1.77 g of (−)-cis-2-(4-hydroxyphenyl)-3-hydroxy-5-[2-(N-methylamino)ethyl]-8-methyl-2,3-dihydro-1,5-benzothiazepin-4(5H)-one.2-(p-hydroxybenzoyl)-benzoate. hydrate are obtained.

M.p. 170°–174° C. (decomp.).
$[\alpha]_D^{20} - 73.14°$ (C=0.35, methanol).

EXAMPLE 35

A mixture of 2.1 g of (±)-cis-2-(4-methoxyphenyl)-3-hydroxy-5-[2-(N-benzyloxycarbonyl-N-methylamino)ethyl]-8-methyl-2,3-dihydro-1,5-benzothiazepin-4(5H)-one, 7 ml of benzene and 7 ml of 25% hydrogen bromide-acetic acid is stirred at room temperature for 2 hours. The mixture is evaporated under reduced pressure at room temperature. Ether is added to the residue, and crystalline precipitates are collected therefrom. The crystals are washed with ether. The crude product (hydrobromide) is converted to its free base, and the resultant free base is converted to its hydrochloride and recrystallized from ethanol. 0.8 g of (±)-cis-2-(4-methoxyphenyl)-3-hydroxy-5-[2-(N-methylamino)ethyl]-8-methyl-2,3-dihydro-1,5-benzothiazepin-4(5H)-one hydrochloride is obtained.

M.p. 230°–232° C. (decomp.).

EXAMPLE 36

(1) 2 g of (±)-cis-2-(4-methylphenyl)-3-hydroxy-8-methyl-2,3-dihydro-1,5-benzothiazepin-4(5H)-one, 0.4 g of potassium hydroxide, 15 ml of dimethylsulfoxide and 2.58 g of 2-(N-benzyloxycarbonyl-N-methylamino)ethyl chloride are treated in the same manner as described in Example 1-(1). 2.6 g of (±)-cis-2-(4-methylphenyl)-3-hydroxy-5-[2-(N-benzyloxycarbonyl-N-methylamino)ethyl]-8-methyl-2,3-dihydro-1,5-benzothiazepine-4(5H)-one are obtained as an oil.

(2) 2.5 g of (±)-cis-2-(4-methylphenyl)-3-hydroxy-5-[2-(N-benzyloxycarbonyl-N-methylamino)ethyl]-8-methyl-2,3-dihydro-1,5-benzothiazepin-4(5H)-one are treated in the same manner as described in Example 35, whereby 1.1 g of (±)-cis-2(4-methylphenyl)-3-hydroxy-5-[2-(N-methylamino)ethyl]-8-methyl-2,3-dihydro-1,5-benzothiazepin-4(5H)-one hydrochloride are obtained.

M.p. 238°–243° C. (recrystallized from dimethylformamide).

EXAMPLE 37

(1) A mixture of 0.97 g of (±)-cis-2-(4-methylphenyl)-3-hydroxy-2,3-dihydro-1,5-benzothiazepin-4(5H)-one, 0.23 g of potassium hydroxide and 15 ml of dimethylsulfoxide is stirred at 50° C. for 30 minutes. A solution of 1.16 g of 2-(N-benzyloxycarbonyl-N-methylamino)ethyl chloride in 5 ml of dimethylsulfoxide is added thereto, and the mixture is stirred at 50° C. for 3 days. After the reaction is completed, the mixture is poured into ice-water and extracted with ethyl acetate. The extract is washed with an aqueous saturated sodium chloride solution, dried and evaporated to remove solvent. The residue is purified by silica gel column chromatography (Solvent:chloroform-ethyl acetate (5:1)), whereby 1.18 g of (±)-cis-2-(4-methylphenyl)-3-hydroxy-5-[2-(N-benzyloxycarbonyl-N-methylamino)ethyl]-2,3-dihydro-1,5-benzothiazepin-4(5H)-one are obtained as an oil.

(2) A mixture of 1.6 g of (±)-cis-2-(4-methylphenyl)-3-hydroxy-5-[2-(N-benzyloxycarbonyl-N-methylamino)ethyl]-2,3-dihydro-1,5-benzothiazepin-4(5H)-one, 3.5 ml of benzene and 2.9 ml of 25% hydrogen bromide-acetic acid is stirred at room temperature for 2 hours. After the reaction is completed, the mixture is diluted with ether. Crystalline precipitates are collected by filtration and recrystallized from ethanol, whereby 956 mg of (±)-cis-2-(4-methylphenyl)-3-hydroxy-5-[2-(N-methylamino)ethyl]-2,3-dihydro-1,5-benzothiazepin-4(5H)-one hydrobromide are obtained as prisms.

M.p. 212°–213° C.

EXAMPLE 38

(1) A mixture of 1.2 g of (±)-cis-2-(4-methylphenyl)-3-hydroxy-5-[2-(N-benzyloxycarbonyl-N-methylamino)ethyl]-2,3-dihydro-1,5-benzothiazepin-4(5H)-one, 5 ml of acetic anhydride and 1 drop of pyridine is heated at 100° C. for 2 hours. After the reaction is completed, the mixture is evaporated to remove acetic acid, acetic anhydride and pyridine. Toluene is added to the residue, and the mixture is evaporated to remove solvent. Toluene is again added thereto and the mixture is evaporated to remove solvent, whereby 1.1 g of (±)-cis-2-(4-methylphenyl)-3-acetoxy-5-[2-(N-benzyloxycarbonyl-N-methylamino)ethyl]-2,3-dihydro-1,5-benzothiazepin-4(5H)-one are obtained as an oil.

(2) A mixture of 1.1 g of (±)-cis-2-(4-methylphenyl)-3-acetoxy-5-[2-(N-benzyloxycarbonyl-N-methylamino)ethyl]-2,3-dihydro-1,5-benzothiazepin-4(5H)-one, 5 ml of acetic acid and 10 ml of 25% hydrogen bromide-acetic acid is stirred at room temperature for 2 hours. After the reaction is completed, the mixture is concentrated under reduced pressure. Toluene is added to the residue, and the mixture is evaporated to remove solvent. Crystalline precipitates are collected by filtration and washed with ether. Then, the crystals are recrystallized from isopropanol. 0.7 g of (±)-cis-2-(4-methylphenyl)-3-acetoxy-5-[2-(N-methylamino)ethyl]-2,3-dihydro-1,5-benzothiazepin-4(5H)-one hydrobromide is obtained as prisms.

M.p. 222°–224° C.

EXAMPLE 39

A mixture of 0.8 g of (±)-cis-2-(4-methylphenyl)-3-acetoxy-5-[2-(N-methylamino)ethyl]-2,3-dihydro-1,5-benzothiazepin- 4(5H)-one hydrobromide, 10 ml of 5% aqueous sodium hydroxide solution and 5 ml of ethanol is stirred at room temperature for 1 hours. After the reaction is completed, the mixture is diluted with water and the aqueous mixture is extracted with chloroform. The extract is washed with aqueous saturated sodium chloride solution, dried and evaporated to remove solvent. The residue is converted to its hydrobromide and recrystallized from ethanol, whereby 0.58 g of (±)-cis-2-(4-methylphenyl)-3-hydroxy-5-[2-(N-methylamino)ethyl]-2,3-dihydro-1,5-benzothiazepin-4(5H)-one hydrobromide is obtained as prisms.

M.p. 212°–213° C.

Preparation of Starting Compounds

Preparation 1

A mixture of 18.2 g of 2-amino-5-methylthiophenol and 25.45 g of methyl (±)-trans-3-(4-methylphenyl)-glycidate is heated at 160° C. for 16 hours under argon gas atmosphere. After cooling, ethanol is added to the mixture. Crystalline precipitates are collected by filtration and recrystallized from a mixture of dimethylformamide and ethanol. 5.15 g of (±)-cis-2-(4-methylphenyl)-3-hydroxy-8-methyl-2,3-dihydro-1,5-benzothiazepin-4(5H)-one are obtained.

M.p. 182.5°–184.5° C.

The following compounds are obtained from the corresponding starting materials in the same manner as above.

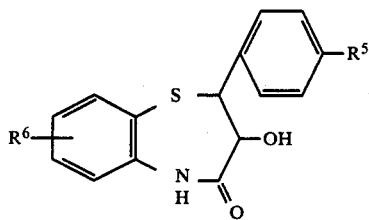

| R⁵ | R⁶ | M.p., etc. |
|---|---|---|
| OCH₃ | 6-OCH₃ | hemihydrate, M.p. 208–210° C. (recrystallized from chloroform-n-hexane) |
| CH₃ | 8-OCH₃ | M.p. 202–206° C. (recrystallized from ethanol) |
| OCH₃ | 8-OCH₂—C₆H₅ | M.p. 172–174° C. (recrystallized from dimethylformamide-ethanol) |
| OCH₃ | 8-CH₃ | M.p. 219–221° C. (recrystallized from dimethylformamide) |
| OCH₃ | 8-F | M.p. 215–218° C. (recrystallized from dimethylformamide-ethanol) |
| OCH₃ | 9-F | M.p. 218–222° C.* |

Note:
The compounds listed in the Table are all (±)-cis-isomers.
*Methyl (±)-threo-2-hydroxy-3-(2-amino-6-fluoro-phenylthio)-3-(4-methoxyphenyl)propionate is obtained in addition to the compound listed above.
M.p. 110–112° C. (recrystallized from ethanol)

Preparation 2

A mixture of 20.66 g of 2-amino-5-fluoro-thiophenol and 27.45 g of methyl (±)-trans-3-(4-methylphenyl)-glycidate is stirred at 150° to 160° C. for 16 hours. After cooling, the mixture is poured into benzene, and 18% hydrochloric acid is added thereto. The organic layer is separated from the mixture, washed with water and an aqueous sodium bicarbonate solution, dried and then evaporated under reduced pressure to remove solvent. The residue is purified by silica gel chromatography (solvent, chloroform:ethyl acetate=10:1) and recrystallized from ethanol. 3.19 g of (±)-cis-2-(4-methylphenyl)-3-hydroxy-8-fluoro-2,3-dihydro-1,5-benzothiazepin-4(5H)-one are obtained.

M.p. 210°–213° C.

2.21 g of (±)-cis-2-(4-methylphenyl)-3-hydroxy-7-methyl-2,3-dihydro-1,5-benzothiazepin-4(5H)-one are obtained from 22.66 g of 2-amino-4-methylthiophenol and 30.97 g of methyl (±)-trans-3-(4-methylphenyl)-glycidate in the same manner as above.

M.p. 204°–205° C.

Preparation 3

(1) A mixture of 29.1 g of 2-amino-5-methylthiophenol, 47.8 g of methyl (±)-trans-3-(4-methoxyphenyl)glycidate and 300 ml of toluene is heated at 60° to 65° C. for 3 days and then at 70° to 80° C. for 2 days. The mixture is evaporated under reduced pressure to remove solvent. Benzene is added to the residue, and the mixture is extracted with conc. hydrochloric acid-water (1:1). The extract is neutralized with potassium carbonate, and the aqueous solution is extracted with benzene. The extract is washed with water, dried and then evaporated under reduced pressure to remove benzene. The residue is purified by silica gel chromatography (solvent, benzen:ethyl acetate=10:1). The resultant product is recrystallized from a mixture of ethanol and isopropyl ether. 15.8 g of methyl (±)-threo-2-hydroxy-3-(2-amino-5-methylphenylthio)-3-(4-methoxyphenyl)propionate are obtained.

M.p. 110°–112° C.

Methyl (±)-threo-2-hydroxy-3-(2-amino-5-methylphenylthio)-3-(4-methylphenyl)propionate is obtained from 2-amino-5-methylthiophenol and methyl (±)-trans-3-(4-methylphenyl)glycidate in the same manner as above.

M.p. 114°–114.5° C. (recrystallized from isopropyl ether).

(2) A mixture of 5 g of methyl (±)-threo-2-hydroxy-3-(2-amino-5-methylphenylthio)-3-(4-methoxyphenyl)-propionate, 50 ml of an aqueous 5% sodium hydroxide solution and 50 ml of methanol is stirred at room temperature for 2 hours. After the reaction is completed, the mixture is adjusted to pH 3 to 5 with 10% hydrochloric acid under ice-cooling. Crystalline precipitates are collected by filtration, washed with water, dried and then recrystallized from methanol. 4.3 g of (±)-threo-2-hydroxy-3-(2-amino-5-methylphenylthio)-3-(4-methoxyphenyl)propionic acid are obtained.

M.p. 190°–193° C.

(±)-threo-2-hydroxy-3-(2-amino-5-methylphenylthio)-3-(4-methylphenyl)propionic acid is obtained from methyl (±)-threo-2-hydroxy-3-(2-amino-5-methylphenylthio)-3-(4-methylphenyl)propionate in the same manner as above.

M.p. 168°–172° C.

(3-a) 45.3 g of L-p-hydroxyphenylglycine methyl ester hydrochloride are dissolved in 1000 ml of methanol. A solution of 11.7 g of potassium hydroxide in 100 ml of methanol is added to said solution under ice-cooling, and the precipitates (potassium chloride) are removed by filtration. 37.8 g of (±)-threo-2-hydroxy-3-(2-amino-5-methylphenylthio)-3-(4-methoxyphenyl)-propionic acid are added to the filtrate. The mixture is warmed to about 50° C., and then 900 ml of methanol are added thereto to make a clear solution. The clear solution is evaporated under reduced pressure at a temperature of below 50° C. 200 ml of ethanol are added to the residue, and the mixture is allowed to stand in a refrigerator overnight. Crystalline precipitates are collected by filtration (The mother liquor is referred as "Mother liquor I"), and then recrystallized from ethanol (The mother liquor is referred as "Mother liquor II".). The crude product thus obtained is further recrystallized from ethanol. 20.7 g of (+)-threo-2-hydroxy-3-(2-amino-5-methylphenylthio)-3-(4-methoxypheyl)propionic acid L-p-hydroxyphenylglycine methyl ester salt (M.p. 164°–167° C., $[\alpha]_D^{20}$255.8° (C=0.66, methanol)) are obtained.

15.3 g of the salt thus obtained are suspended in a mixture of 240 ml of methanol and 200 ml of water, and 27 ml of cation exchange resin are added thereto. The mixture is stirred at room temperature overnight. The resin is removed by filtration and washed with methanol. The filtrate and the washings are combined and evaporated under reduced pressure to remove solvent. Water is added to the residue. The precipitated crystals are collected by filtration and then recrystallized from ethanol. 7 g of (+)-threo-2-hydroxy-3-(2-amino-5-methylphenylthio)-3-(4-methoxyphenyl)propionic acid are obtained.

M.p. 158°–160° C.
$[\alpha]_D^{20}$ +296.0° (C=0.29, methanol).

Mother liquors I and II are combined, and 13 ml of conc. hydrochloric acid are added thereto. The mixture is evaporated under reduced pressure to remove solvent. Water is added to the residue, and crystalline precipitates are collected by filtration. Then, the crystals (15.5 g) thus obtained, 20.3 g of D-p-hydroxyphenylglycine methyl ester hydrochloride and 5.2 g of potassium hydroxide are treated in the same manner as above. 12.9 g of (−)-threo-2-hydroxy-3-(2-amino-5-methylphenylthio)-3-(4-methoxyphenyl)propionic acid D-p-hydroxyphenylglycine methyl ester salt (M.p. 164°–167° C., recrystallized from ethanol, $[\alpha]_D^{20} -254.8°$ (C=0.95, methanol)) are obtained.

The salt (15.3 g) thus obtained are then converted to its free acid in the same manner as above. 6.5 g of (−)-threo-2-hydroxy-3-(2-amino-5-methylphenylthio)-3-(4-methoxyphenyl)propionic acid are obtained.

M.p 158°–160° C. (recrystallized from ethanol).
$[\alpha]_D^{20} -265 3°$ (C=0.33, methanol).

(3-b) A solution of 0.71 g of potassium hydroxide in 10 ml of methanol is gradually added to a solution of 2.74 g of L-p-hydroxyphenylglycine methyl ester hydrochloride in 70 ml of methanol. Insoluble materials are removed by filtration and washed with methanol. The filtrate and washings are combined, and 2 g of (±)-threo-3-(2-amino-5-methylphenylthio)-2-hydroxy-3-(4-methylphenyl)propionic acid are added thereto. The mixture is evaporated under reduced pressure to remove methanol. 20 ml of ethanol are added to the residue, and the mixture is allowed to stand at 0° C. overnight. Crystalline precipitates are collected by filtration and recrystallized twice from ethanol. 0.41 g of (+)-threo-3-(2-amino-5-methylphenylthio)-2-hydroxy-3-(4-methylphenyl)propionic acid L-p-hydroxyphenylglycine methyl ester salt is obtained.

M.p 170°–172° C.
$[\alpha]_D^{20} +308.64°$ (C=0.61, methanol).

A mixture of 2.65 g of the salt thus obtained and 10 ml of 10% hydrochloric acid is evaporated under reduced pressure to remove solvent. Water is added to the residue, and the mixture is evaporated under reduced pressure to remove solvent. Water is added to the residue, and crystalline precipitates are collected by filtration. The crystals are washed with water, dried and then recrystallized from methanol. 0.93 g of (+)-threo-3-(2-amino-5-methylphenylthio)-2-hydroxy-3-(4-methylphenyl)propionic acid is obtained.

M.p. 166°–168° C.
$[\alpha]_D^{20} +356.7°$ (C=0.52, dimethylformamide).

2.75 g of potassium hydroxide, 10.65 g of D-p-hydroxy-phenylglycine methyl ester hydrochloride and 7.77 g of (±)-threo-3-(2-amino-5-methylphenylthio)-2-hydroxy-3-(4-methylphenyl)propionic acid are treated in the same manner as above, whereby 1.21 g of (−)-threo-3-(2-amino-5-methylphenylthio)-2-hydroxy-3-(4-methylphenyl)propionic acid D-p-hydroxyphenylglycine methyl ester salt are obtained.

M.p. 170°–172° C. (recrystallized from ethanol).
$[\alpha]_D^{20} -320.61°$ (C=0.41, methanol).

0.39 g of (−)-threo-3-(2-amino-5-methylphenylthio)-2-hydroxy-3-(4-methylphenyl)propionic acid is obtained from 1.18 g of the thus-obtained salt in the same manner as above.

M.p. 166°–168° C. (recrystallized from methanol).
$[\alpha]_D^{20} -356.23°$ (C=0.63, dimethylformamide).

(4) A mixture of 9 g of (+)-threo-2-hydroxy-3-(2-amino-5-methylphenylthio)-3-(4-methoxyphenyl)propionic acid and 350 ml of xylene is refluxed for 24 hours. The resultant water is removed during the reaction. After the reaction is completed, the mixture is evaporated under reduced pressure to remove xylene, and the residue is recrystallized from ethyl acetate. 7.8 g of (+)-cis-2-(4-methoxyphenyl)-3-hydroxy-8-methyl-2,3-dihydro-1,5-benzothiazepin-4(5H)-one are obtained.

M.p. 223°–226° C. (decomp.).
$[\alpha]_D^{20} +123.8°$ (C=0.71, dimethylformamide).

The following compounds are obtained from the corresponding starting materials in the same manner as above.

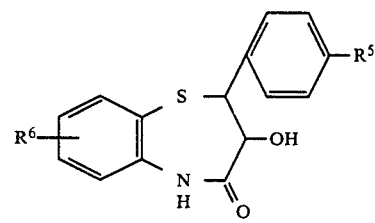

| $R^5$ | $R^6$ | Optical isomer | M.p., etc. |
|---|---|---|---|
| OCH₃ | 8-CH₃ | — | M.p. 224–226° C. (decomp.) (recrystallized from ethyl acetate) $[\alpha]_D^{20} - 123.7°$ (C = 0.41, dimethylformamide) |
| CH₃ | 8-CH₃ | + | M.p. 212–215° C. (recrystallized from ethanol) $[\alpha]_D^{20} + 122.72°$ (C = 0.31, methanol) |
| CH₃ | 8-CH₃ | − | M.p. 214–215° C. (recrystallized from ethanol) $[\alpha]_D^{20} - 125.96$ (C = 0.26, methanol) |

Note:
The compounds listed in the Table are all cis isomer.

Preparation 4

(1) The following compounds are obtained from the corresponding starting materials in the same manner as described in preparation 3-(1).

(i) Methyl (±)-threo-2-hydroxy-3-(2-amino-5-methylthiophenylthio)-3-(4-methoxyphenyl)propionate
M.p. 114°–116° C. (recrystallized from ethanol).

(ii) Methyl (±)-threo-2-hydroxy-3-(2-amino-4-methylthiophenylthio)-3-(4-methoxyphenyl)propionate
M.p. 130°–132° C. (recrystallized from ethanol).

(2) A mixture of 1.5 g of sodium hydride (63% oil dispersion) and 25 ml of dimethylsulfoxide is heated at 70° C. for 50 minutes in argon atmosphere. A solution of 7 g of methyl (±)-threo-2-hydroxy-3-(2-amino-5-methylthio-phenylthio)-3-(4-methoxyphenyl)propionate in 12 ml of dimethylsulfoxide is added dropwise to the mixture under cooling. The mixture is stirred at room temperature for 20 minutes. After the reaction is completed, the mixture is poured into ice-water. Crystalline precipitates are collected by filtration, washed with water, dried and then recrystallized from a mixture of dimethylformamide and ethanol. 6.7 g of (±)-cis-2-(4-methoxyphenyl)-3-hydroxy-8-methylthio-2,3-dihydro-1,5-benzothiazepin-4(5H)-one are obtained.

M.p. 183°–184° C.

The following compounds are obtained from the corresponding starting materials in the same manner as above.

(i) (±)-cis-2-(4-methoxyphenyl)-3-hydroxy-7-methylthio-2,3-dihydro-1,5-benzothiazepin-4(5H)-one
M.p. 211°–214° C. (recrystallized from dimethylformamide-ethanol).

(ii) (±)-cis-2-(4-methoxyphenyl)-3-hydroxy-9-fluoro-2,3-dihydro-1,5-benzothiazepin-4(5H)-one M.p. 217°–220° C. (recrystallized from dimethylformamide-ethanol).

What we claim is:

1. A 1,5-benzothiazepine of the formula:

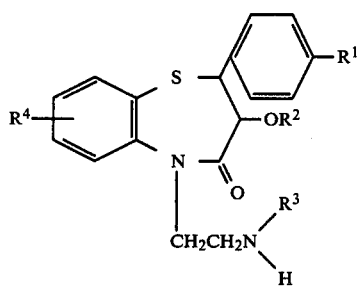

wherein
R$^1$ is lower alkyl or lower alkoxy;
R$^2$ is hydrogen or lower alkanoyl;
R$^3$ is lower alkyl; and
R$^4$ is lower alkyl or lower alkoxy; or a pharmaceutically acceptable acid addition salt thereof.

2. A compound claimed in claim 1, in which R$^1$ is lower alkyl.

3. A compound claimed in claim 1, in which R$^4$ is lower alkyl.

4. A compound claimed in claim 1, in which R$^1$ is lower alkyl and R$^4$ is lower alkyl.

5. A compound claimed in claim 1, in which R$^1$ is methyl or methoxy, R$^2$ is hydrogen or acetyl, R$^3$ is methyl and R$^4$ is methyl or methoxy.

6. A compound claimed in claim 2, in which R$^1$ is methyl R$^2$ is hydrogen or acetyl, R$^3$ is methyl and R$^4$ is methyl or methoxy.

7. A compound claimed in claim 3, in which R$^1$ is methyl or methoxy, R$^2$ is hydrogen or acetyl, R$^3$ is methyl, and R$^4$ is methyl.

8. A compound claimed in claim 4, in which R$^1$ is methyl, R$^2$ is hydrogen or acetyl, R$^3$ is methyl and R$^4$ is methyl and is in the 8-position of benzothiazepine skeleton.

9. A cis isomer of a compound claimed in claim 1.
10. A cis isomer of a compound claimed in claim 2.
11. A cis isomer of a compound claimed in claim 4.
12. A cis isomer of a compound claimed in claim 8.
13. A cis isomer of a compound claimed in claim 1.
14. A (−)-cis isomer of the compound claimed in claim 8.

15. The compound of claim 8, which is (−)-cis-2-(4-methylphenyl)-3-hydroxy-5-[2-(N-methylamino)ethyl]-8-methyl-2,3-dihydro-1,5-benzothiazepin-4(5H)-one or a pharmaceutically acceptable acid addition salt thereof.

16. The compound of claim 8, which is (±)-cis-2-(4-methylphenyl)-3-hydroxy-5-[2-(N-methylamino)ethyl]-8-methyl-2,3-dihydro-1,5-benzothiazepin-4(5H)-one or a pharmaceutically acceptable acid addition salt thereof.

17. The compound according to claim 1 which is (+)-cis-2-(4-methylphenyl)-3-hydroxy-5-[2-(methylamino)ethyl]-8-methoxy-2,3-dihydro-1,5-benzothiazepin-4(5H)-one or a pharmaceutically aceeptable acid addition salt thereof.

18. The compound according to claim 1 which is (±)-cis-2-(4-methylphenyl)-3-acetoxy-5-[2-(methylamino)ethyl]-8-methoxy-2,3-dihydro-1,5-benzothiazepin-4 (5H)-one or a pharmaceutically acceptable acid addition salt thereof.

19. The compound according to claim 1 which is (±)-cis-2-(4-methylphenyl)-3-acetoxy-5-[2-(methylamino)ethyl]-8-methyl-2,3-dihydro-1,5-benzothiazepin-4(5H)-one or a pharmaceutically acceptable acid addition salt thereof.

20. The compound according to claim 1 which is (−)-cis-2-(4-methylphenyl)-3-hydroxy-5-[2-(methylamino)ethyl]-8-methyl-2,3-dihydro-1,5-benzothiazepin-4(5H)-one or a pharmaceutically acceptable acid addition salt thereof.

21. A pharmceutical composition possessing platelet aggregation-inhibiting activity, which comprises as the essential active ingredient, a therapeutically effective amount of a compound claimed in claim 1 in admixture with a conventional pharmaceutically acceptable carrier or diluent.

22. The pharmaceutical composition according to claim 21, wherein the essential active ingredient is a compound as claimed in claim 2.

23. The pharmaceutical composition according to claim 21, wherein the essential active ingredient is a compound as claimed in claim 8.

24. A method of producing a platelet aggregation-inhibiting effect on a warm-blooded animal comprising administering to said warm-blooded animal an effective amount of a compound claimed in claim 1.

* * * * *

UNITED STATES PATENT AND TRADEMARK OFFICE
CERTIFICATE OF CORRECTION

PATENT NO. : 4,594,342

DATED : June 10, 1986

INVENTOR(S) : Mikio Takeda, et al.

It is certified that error appears in the above-identified patent and that said Letters Patent is hereby corrected as shown below:

Column 4, line 47: "Q" should be --H--

Signed and Sealed this

First Day of September, 1987

*Attest:*

DONALD J. QUIGG

*Attesting Officer*  *Commissioner of Patents and Trademarks*